(12) United States Patent
Murphy et al.

(10) Patent No.: US 10,551,291 B2
(45) Date of Patent: Feb. 4, 2020

(54) BALANCED CAPILLARY BRIDGE VISCOMETRY

(71) Applicant: Malvern Panalytical Inc., Westborogh, MA (US)

(72) Inventors: Michael P. Murphy, West Conroe, TX (US); Mark Nicholls, Houston, TX (US)

(73) Assignee: Malvern Panalytical Inc., Westborough, MA (US)

( * ) Notice: Subject to any disclaimer, the term of this patent is extended or adjusted under 35 U.S.C. 154(b) by 0 days.

(21) Appl. No.: 15/701,043

(22) Filed: Sep. 11, 2017

(65) Prior Publication Data

US 2018/0106710 A1    Apr. 19, 2018

Related U.S. Application Data

(62) Division of application No. 13/825,622, filed as application No. PCT/GB2011/051805 on Sep. 23, 2011, now Pat. No. 9,759,644.

(Continued)

(51) Int. Cl.
*G01N 11/00* (2006.01)
*G01N 11/02* (2006.01)
(Continued)

(52) U.S. Cl.
CPC ............ *G01N 11/08* (2013.01); *G01N 11/02* (2013.01); *G01N 11/04* (2013.01); *G01N 11/06* (2013.01);
(Continued)

(58) Field of Classification Search
CPC ................................. G01N 11/08; G01N 11/04
See application file for complete search history.

(56) References Cited

U.S. PATENT DOCUMENTS 2,449,067 A    9/1948   Guillemin
3,086,386 A    4/1963   Frederick
(Continued)

FOREIGN PATENT DOCUMENTS

JP    S59160740    10/1983
JP    2006276018   10/2006
JP    2009133726   6/2009

OTHER PUBLICATIONS

PCT International Search Report.
(Continued)

*Primary Examiner* — Paul M. West
(74) *Attorney, Agent, or Firm* — Kristofer E. Elbing

(57) ABSTRACT

Viscometers and Viscometry methods are disclosed. In one general aspect a capillary bridge viscometer comprises an input port an output port a first capillary tubing arm in a first hydraulic path between the input port and a first differential detection point, a second capillary tubing arm in a second hydraulic path between the first differential detection point and the output port, a third capillary tubing arm in a third hydraulic path between the input port and a second differential detection point, a fourth capillary tubing arm in a fourth hydraulic path between the second differential detection point and the output port, an adjustable mechanical flow restrictor in one of the first, second, third, and fourth hydraulic paths, wherein the adjustable mechanical flow restrictor is operative to mechanically adjust a resistance to flow of a fluid while the fluid flows through the adjustable mechanical flow restrictor.

22 Claims, 2 Drawing Sheets

Related U.S. Application Data

(60) Provisional application No. 61/385,952, filed on Sep. 23, 2010.

(51) Int. Cl.
  *G01N 11/04* (2006.01)
  *G01N 11/06* (2006.01)
  *G01N 11/14* (2006.01)
  *G01N 11/08* (2006.01)

(52) U.S. Cl.
  CPC .............. *G01N 2011/0006* (2013.01); *G01N 2011/0093* (2013.01); *G01N 2011/147* (2013.01)

(56) References Cited

U.S. PATENT DOCUMENTS

| | | |
|---|---|---|
| 3,302,448 A | 2/1967 | Mocker |
| 4,463,598 A | 8/1984 | Haney |
| 4,779,642 A | 10/1988 | Wood |
| 6,561,480 B1 | 5/2003 | Komiya |
| 7,213,439 B2 | 5/2007 | Trainoff |
| 7,331,218 B2 | 2/2008 | Trainoff |
| 9,759,644 B2 * | 9/2017 | Nicholls ................ G01N 11/08 |
| 2002/0166367 A1 | 11/2002 | Bures |
| 2007/0068229 A1 | 3/2007 | Trainoff |

OTHER PUBLICATIONS

PCT Written Opinion.
apanese Office Action, dated Apr. 25, 2016.
Communication about intention to grant a European patent, including text intended for grant, dated Sep. 11, 2018.

\* cited by examiner

BALANCED CAPILLARY BRIDGE VISCOMETRY

CROSS-REFERENCE TO RELATED APPLICATIONS

This application is a continuation of U.S. patent application Ser. No. 13/825,622 (U.S. Pat. No. 9,759,644), which is a National Stage entry of PCT/GB2011/051805, filed Sep. 23, 2011, which, in turn, claims priority to U.S. provisional patent application No. 61/385,952, filed Sep. 23, 2010. All of these applications are herein incorporated by reference.

FIELD OF THE INVENTION

The invention relates, in one general aspect, to capillary viscometers, including capillary bridge viscometers that include an automatic balancing mechanism.

BACKGROUND OF THE INVENTION

Referring to FIG. 1, multi-capillary viscometers can introduce some type of delay unit in order to make a differential measurement while a sample is being measured. An illustrative prior art four-capillary viscometer 10, for example, includes four pieces of tubing or capillaries connected in a series-parallel configuration to form the hydraulic equivalent of a Wheatstone-Bridge in electronics. These tubing or capillaries in the arms of the bridge are often referred to as R1, R2, R3, and R4 because they are in effect hydraulic resistors. The delay unit 12 is placed in series with one of the capillaries and usually it consists of a column packed with or containing a material or solvent that will delay the sample from reaching a reference capillary while a measurement is taking place. This delay unit should generally provide for sufficient time or volume to accommodate the entire elution volume of the analytical GPC (Gel Permeation Chromatography) column set that is used for the separation analysis. In liquid chromatography there are a vast number of column set configurations, many requiring different delay volumes. Initially, the capillary configuration is arranged such that the "bridge" is "balanced" meaning that the DP+ & DP− readings are approximately equal.

In the illustrative viscometer, R1, R2, R3, and R4 are capillary tubes of a small diameter giving them a measurable resistance to the solvent flow, and if R1=R2=R3=R4, the differential pressure (DP) output should theoretically be zero. This is the output signal from the bridge and should be within a small percentage of the total pressure across the bridge measured between the two differential measurement points IP+ and IP− when solvent is flowing. This is called the bridge balance and is given by the equation, Balance=4DP/IP-2DP, where DP is the differential signal from the DP+ and DP− readings measured in Pascals and IP is as mentioned above measured in kPa. Capillary bridge viscometers are described in more detail, for example, in U.S. Pat. No. 4,463,598 to Haney, which is herein incorporated by reference.

When a delay volume is placed in series with one or more capillaries, the bridge can be balanced or rebalanced to make up for additional resistance introduced by the presence of the delay volume(s). This can be accomplished by adjusting the length(s) of one or more of the capillary tubing runs to get the bridge balance back to the manufacturing standard balance. Upon installation or during use, it may become necessary to adjust this delay volume according to the analytical column set required for analysis. One or more additional delay volumes of different sizes may therefore be shipped with the instrument or purchased to meet the specific need of the customer. With these changes comes either increased or decreased resistance within the combined capillary and delay column flow path, and the viscometer can be rebalanced by adding or subtracting to the length of the appropriate capillary tubing in order to achieve the most efficient performance by returning to a balanced condition.

The traditional method for balancing a viscometer bridge is to change the length of one or more of the capillary flow paths. This is accomplished by calculating the amount to subtract (or add) from a length of one or more of the capillaries. The bridge is then disassembled to make the change and reassembled by a skilled technician. This can be extremely inconvenient and may also require the instrument to be returned to the manufacturer for qualified servicing. It is also common for the balance to change due to the introduction of different solvents. These changes are typically ignored because of the inconvenience and because the length difference involved can be physically too small to allow an accurate adjustment to be accurately accomplished, and the result can be a decrease in instrument performance.

Temperature-based balancing has also been proposed in U.S. Pat. No. 7,213,439 to Trainoff, which is herein incorporated by reference. But this approach can have the potential drawback of causing thermally induced changes to properties of the fluids in the viscometer. Understanding whether such changes are a concern for a particular experimental setup and whether they should possibly be compensated for can introduce the prospect of an undesirable level of theoretical complexity for the end user of the viscometer.

SUMMARY OF THE INVENTION

Several aspects of the invention are presented in this application.

DETAILED DESCRIPTION OF AN ILLUSTRATIVE EMBODIMENT

Figure 1:
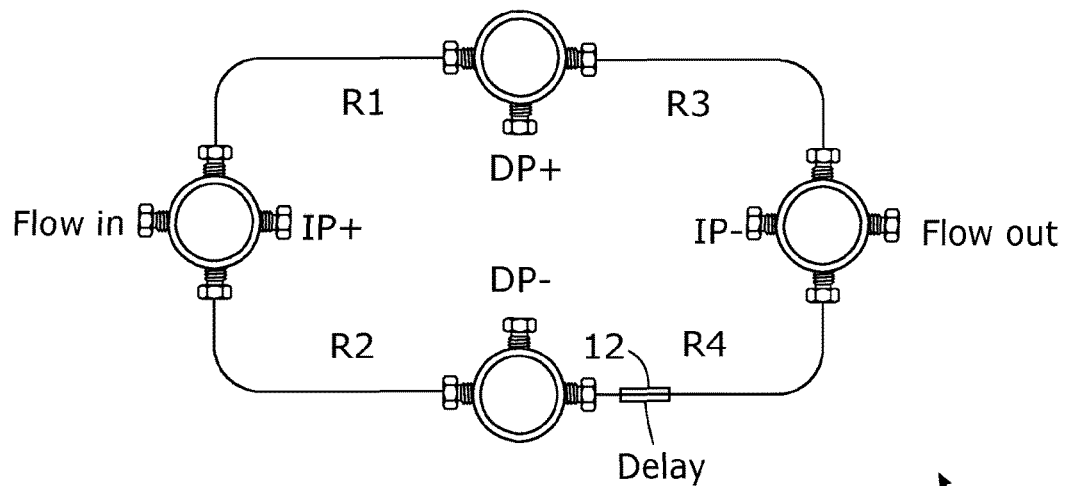
FIG. 1 is a hydraulic schematic diagram of a prior art capillary bridge viscometer.
Figure 2:
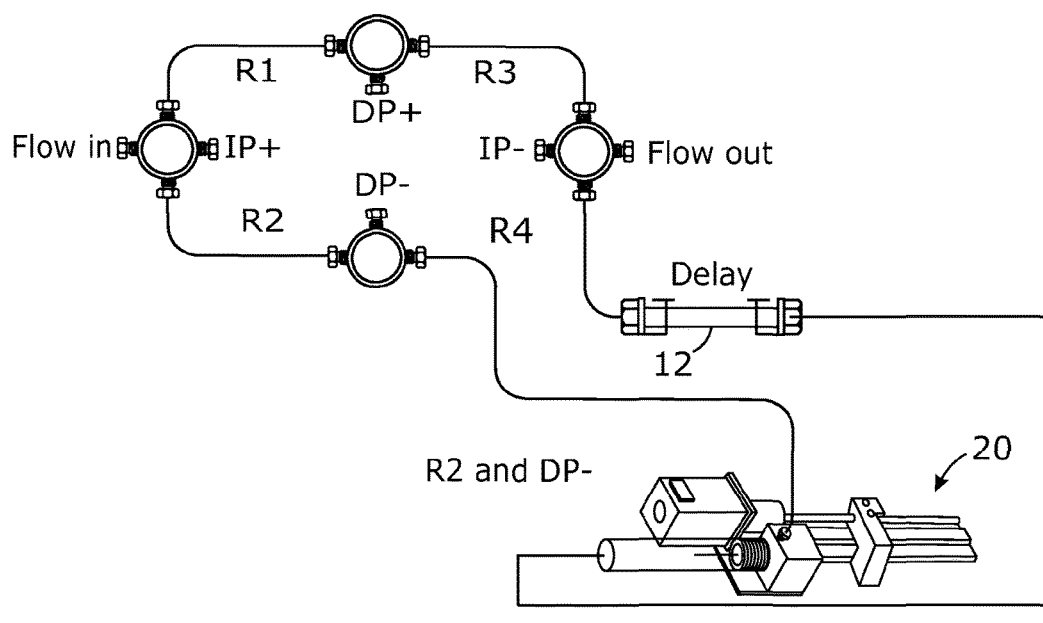
FIG. 2 is a hydraulic schematic diagram of an illustrative capillary bridge viscometer according to the invention.

Referring to FIG. 2, an illustrative capillary bridge viscometer 14 according to the invention includes a bridge 10 with a mechanical balancing unit 20 that can be placed in series with its delay line 12. One of the capillaries is made shorter than it otherwise would at the time of assembly such that the reduction in length is approximately equal to the resistance of the mechanical balancing unit. This allows the illustrative viscometer to overcome normal changes in bridge balance it experiences.

Figure 3:
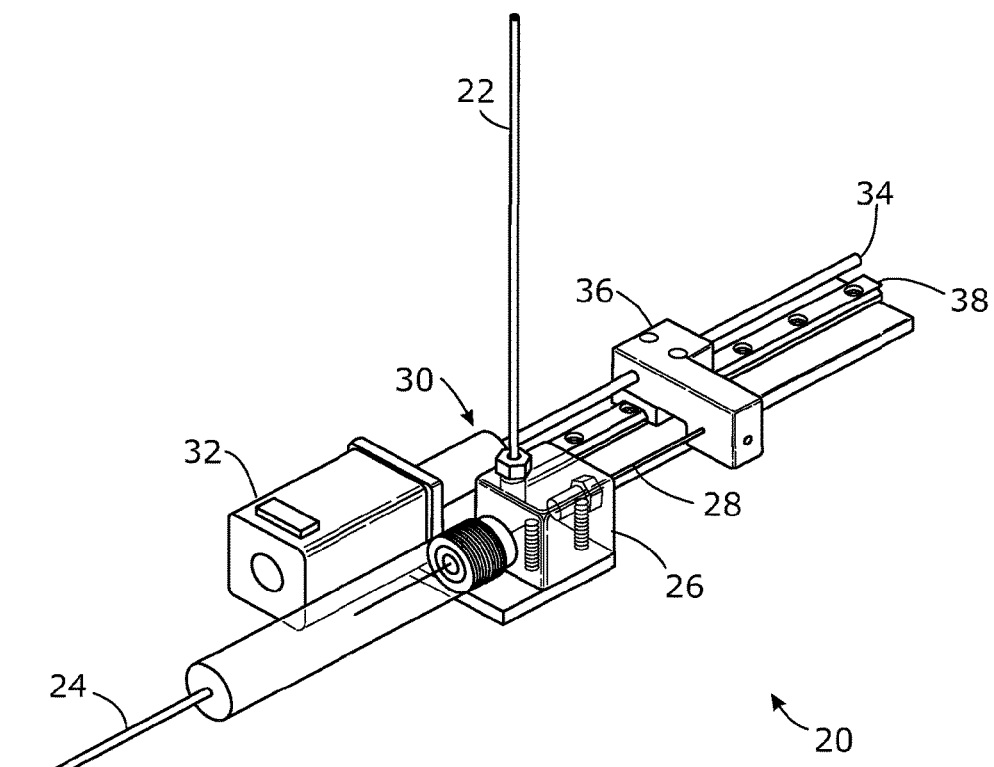
FIG. 3 is a perspective diagram of a mechanical balancing unit for use with the illustrative capillary bridge viscometer of FIG. 2.

Referring to FIG. 3, the mechanical balancing unit 20 includes a first conduit 22 that is hydraulically connected to a second conduit 24, such as through a machined plumbing block 26, which can be made out of a relatively unreactive material such as stainless steel. A movable solid core 28, which can include a straight length of cylindrical Nitinol® rod, is threaded through the second conduit. This second conduit has a calculated diameter large enough to accept the core with the resulting resistance to solvent flow being approximately equal to the corresponding portion of the capillary. The Nitinol rod may be supported by a metal tube to prevent movement and sealed to the machined block with a fitting that allows plumbing connection to the rest of the bridge. The Nitinol rod can then be mounted on an actuating mechanism 30, inserted through a seal, and passed into the tubing. The seal can be one of a variety of types of seals, such as an o-ring or seal made with a length of 0.03" Teflon® tubing. The second conduit can be supported by a support structure, such as a threaded aluminum support tube 25.

The actuating mechanism 30 can move the Nitinol rod in and out of the second conduit to change the pressure across the mechanical balancing unit. The actuating mechanism 30 in the illustrative embodiment can be a linear actuating mechanism that includes a motor 32, such as a stepper motor, that drives a lead screw 34 to advance a carriage 36 on a track 38. Other embodiments can employ a variety of other mechanisms to adjust resistance to flow, such as linkages, racks-and-pinions, magnetically coupled linear actuators, or cam-based mechanisms. And while the use of a machined plumbing block with standard fittings is presently preferred to allow movement of the core without leakage, one of ordinary skill in the art would readily recognize that other approaches could also be employed to achieve the same end. The complete assembly can be mounted on a mounting plate for stability.

Figure 4:
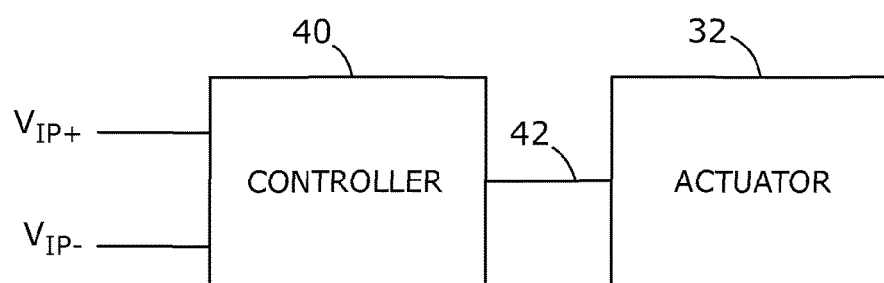
FIG. 4 is a block diagram of a control arrangement for controlling the mechanical balancing unit of FIG. 3.

Referring also to FIG. 4, a controller 40 may be provided to drive the actuator. This controller can employ a variety of known control techniques. It can employ dedicated hard-wired circuitry, software, or a combination of the two.

Operation begins with a solvent being introduced into the bridge viscometer 14. The differential pressure between the two intermediate measurement points DP+ and DP− is measured to determine whether the bridge is in balance. If it is not, the mechanical balancing unit is adjusted by moving the core in or out of the second conduit to balance the bridge.

The Nitinol rod and carriage assembly are situated in relation to the plumbing block such that, when the rod is pulled all the way out, the resistance of the bridge balance device has almost no resistance to fluid flow. As the rod is pushed into the tube the effective diameter of the tube is decreased, which increases the resistance of the flow path containing the device and capillary. This is in essence the same as adding to the length of the capillary. Conversely, drawing the rod back out of the tube reduces the resistance in the flow path containing the device and capillary. This allows the user to obtain excellent precision in viscometer balance and performance.

The adjustment may be performed automatically, semi-automatically, or manually. In automatically balanced embodiments, a controller can detect an imbalance between signals from transducers that measure the two intermediate measurement points DP+ and DP−. The controller can then produce a driving signal 42 that it provides to the actuator 32 until the imbalance is resolved. In semi-automatically balanced embodiments, an operator can provide a signal to the actuator until he or she determines that the bridge is balanced. In a manually balanced embodiment, no actuator is needed and the user can balance the bridge mechanically, such as by manually turning a knob attached to the lead screw 34. All of these methods are less cumbersome than prior art methods that involve replacing lengths of capillary tubing and can be readily performed in situ by the customer.

The mechanical balancing unit mechanism described above has been found to allow very fine pressure adjustments. This can allow for the construction of a highly precise instrument. A variety of other types of balancing unit mechanisms, such as ones based on micrometering valves or ones that that operate by squeezing or stretching flexible tubing, may also be suitable in some circumstances.

The mechanical balancing unit can be used in a variety of different kinds of instruments. It can be used in a more complex capillary viscometer that provides for eliminating break through peaks, for example, such as is described in US Pub. No. 2008/045133 to Titterton, which is herein incorporated by reference. It can also be used in other types of instruments that benefit from the ability to make small changes in flow resistance.

The present invention has now been described in connection with a number of specific embodiments thereof. However, numerous modifications which are contemplated as falling within the scope of the present invention should now be apparent to those skilled in the art. Therefore, it is intended that the scope of the present invention be limited only by the scope of the claims appended hereto. In addition, the order of presentation of the claims should not be construed to limit the scope of any particular term in the claims.

What is claimed is:

1. A method of operating a capillary bridge viscometer, comprising:
   providing a capillary bridge viscometer, comprising:
      an input port,
      an output port,
      a first capillary tubing arm in a first hydraulic path between the input port and a first differential detection point,
      a second capillary tubing arm in a second hydraulic path between the first differential detection point and the output port,
      a third capillary tubing arm in a third hydraulic path between the input port and a second differential detection point,
      a fourth capillary tubing arm in a fourth hydraulic path between the second differential detection point and the output port, and
      an adjustable mechanical flow restrictor in one of the first, second, third, and fourth hydraulic paths, wherein the adjustable mechanical flow restrictor is operative to mechanically adjust a resistance to flow of a fluid while the fluid flows through the adjustable mechanical flow restrictor,
      a delay volume in series with one of the first to fourth capillary tubing arms and separate from the adjustable mechanical flow restrictor,
   introducing a solvent into the capillary bridge viscometer,
   splitting the flow of solvent to direct a first portion of the solvent through the first capillary tubing arm, and to direct a corresponding second portion of the solvent through the second capillary tubing arm,
   measuring a differential pressure between the first and second differential detection points to determine whether the bridge is in balance,
   if the bridge is not in balance, adjusting the mechanical flow restrictor to balance the bridge while it remains in the bridge,
   delaying one of the first and second corresponding portions of the flow of solvent in the delay volume, and
   making a differential pressure measurement for the other of the first and second corresponding portions of the flow of solvent during the step of delaying.

2. A method of operating a capillary bridge viscometer, comprising:
 providing a capillary bridge viscometer, comprising:
  an input port,
  an output port,
  a first capillary tubing arm in a first hydraulic path between the input port and a first differential detection point,
  a second capillary tubing arm in a second hydraulic path between the first differential detection point and the output port,
  a third capillary tubing arm in a third hydraulic path between the input port and a second differential detection point,
  a fourth capillary tubing arm in a fourth hydraulic path between the second differential detection point and the output port, and
  an adjustable mechanical flow restrictor in one of the first, second, third, and fourth hydraulic paths, wherein the adjustable mechanical flow restrictor is operative to mechanically adjust a resistance to flow of a fluid while the fluid flows through the adjustable mechanical flow restrictor, and
  a delay line in series with one of the first to fourth capillary tubing arms, wherein the delay line and that one capillary tubing arm provide a substantially larger time or volume in one of the paths between the input port and the output port than does one of the capillary tubing arms in the other of the paths, and wherein the delay line is separate from the adjustable mechanical flow restrictor,
 introducing a solvent into the capillary bridge viscometer,
 measuring a differential pressure between the first and second differential detection points to determine whether the bridge is in balance, and
 if the bridge is not in balance, adjusting the mechanical flow restrictor to balance the bridge.

3. The method of claim 2 wherein the step of adjusting adjusts the mechanical flow restrictor using an actuator.

4. The method of claim 2 wherein the step of measuring a differential pressure is performed using a balance detector operatively connected between the first and second differential detection points.

5. The method of claim 2 wherein the mechanical flow restrictor is adjusted by a controller responsive to the balance detector that detects an imbalance in the bridge and produces a driving signal to an actuator to adjust the mechanical flow restrictor until the balance is resolved.

6. The method of claim 2 wherein the mechanical flow restrictor is adjusted by a controller that detects an imbalance in the bridge and produces a driving signal to an actuator to adjust the mechanical flow restrictor until the balance is resolved.

7. The method of claim 2 further including providing a second adjustable mechanical flow restrictor in another of the first, second, third, and fourth hydraulic paths, wherein the second adjustable mechanical flow restrictor is operative to mechanically adjust a resistance to flow of a fluid while the fluid flows through the second adjustable mechanical flow restrictor and further including the step of adjusting the second adjustable mechanical flow restrictor.

8. The method of claim 2 wherein the step of adjusting includes translating a solid cylindrical core inside a cylindrical tube along a fluid flow path that follows the fluid flow axis.

9. The method of claim 2 wherein the step of adjusting includes translating a solid cylindrical core inside a tube using a translating mechanism.

10. The method of claim 2 wherein the step of adjusting includes translating a solid cylindrical core inside a cylindrical tube along a flow axis located at the center of the tube using a translating mechanism.

11. The method of claim 2 wherein the step of adjusting includes translating a solid cylindrical core inside a tube using a motor and a lead screw.

12. The method of claim 2 wherein the steps of introducing, measuring, and adjusting are performed as part of a liquid chromatography separation analysis.

13. The method of claim 12 wherein the delay line generally provides for sufficient time or volume to accommodate the entire elution volume for the separation analysis.

14. The method of claim 2 further including:
 changing one of the capillary tubing arms after the step of adjusting,
 again measuring a differential pressure between the first and second differential detection points to determine whether the bridge is in balance, and
 if the bridge is not in balance, again adjusting the mechanical flow restrictor to balance the bridge and thereby compensate for the change in the capillary tubing arms.

15. The method of claim 14 wherein the step of making a differential pressure measurement is performed as part of a liquid chromatography separation analysis and wherein the delay line generally provides for sufficient time or volume to accommodate the entire elution volume for the separation analysis.

16. The method of claim 2 wherein the delay line includes a column that includes column that includes a material or solvent to delay the sample while a measurement is taking place.

17. The method of claim 2 further including:
 changing the delay line after the step of adjusting,
 again measuring a differential pressure between the first and second differential detection points to determine whether the bridge is in balance, and
 if the bridge is not in balance, again adjusting the mechanical flow restrictor to balance the bridge and thereby compensate for the change in the delay line.

18. The method of claim 17 wherein the step of making a differential pressure measurement is performed as part of a liquid chromatography separation analysis and wherein the delay line generally provides for sufficient time or volume to accommodate the entire elution volume for the separation analysis.

19. The method of claim 2 further including:
 again measuring a differential pressure between the first and second differential detection points to determine whether the bridge is in balance, and
 if the bridge is not in balance, again adjusting the mechanical flow restrictor to balance the bridge.

20. The method of claim 19 wherein the step of making a differential pressure measurement is performed as part of a liquid chromatography separation analysis and wherein the delay line generally provides for sufficient time or volume to accommodate the entire elution volume for the separation analysis.

21. The method of claim 20 wherein the delay line includes a column that includes a material or solvent to delay the sample while a measurement is taking place.

22. The method of claim 2 wherein the step of providing a delay line provides a delay line that provides a substantially larger time or volume in one of the paths between the input port and output port than do the capillary tubing arms in the other of the paths.

\* \* \* \* \*

UNITED STATES PATENT AND TRADEMARK OFFICE
CERTIFICATE OF CORRECTION

PATENT NO. : 10,551,291 B2
APPLICATION NO. : 15/701043
DATED : February 4, 2020
INVENTOR(S) : Michael P. Murphy and Mark Nicholls It is certified that error appears in the above-identified patent and that said Letters Patent is hereby corrected as shown below:

On the Title Page

Page 2, Line 26, "apanese" should read --Japanese--

In the Claims

Column 6, Line 34, Claim 16, Line 2, "a column that includes column that includes a material" should read --a column that includes a material--

Signed and Sealed this
Twelfth Day of May, 2020

Andrei Iancu
*Director of the United States Patent and Trademark Office*